United States Patent [19]
Mazanek et al.

[11] Patent Number: 5,936,019
[45] Date of Patent: Aug. 10, 1999

[54] POLYURETHANE-BASED THICKENER COMPOSITIONS AND THEIR USE FOR THICKENING AQUEOUS COMPOSITIONS

[75] Inventors: Jan Mazanek, Köln; Hermann Kober, Bergisch Gladbach; Klaus Walz, Leverkusen, all of Germany

[73] Assignee: Bayer Aktiengesellschaft, Leverkusen, Germany

[21] Appl. No.: 08/907,671

[22] Filed: Aug. 8, 1997

[30] Foreign Application Priority Data

Aug. 19, 1996 [DE] Germany ............... 196 33 195

[51] Int. Cl.$^6$ ............... C08J 3/00; C08K 3/20; C08K 5/06; C08L 75/00
[52] U.S. Cl. ............... 524/366; 524/375; 524/590; 524/591; 524/839; 524/840
[58] Field of Search ............... 524/590, 591, 524/839, 840, 366, 375

[56] References Cited

U.S. PATENT DOCUMENTS

| | | | |
|---|---|---|---|
| 3,362,780 | 1/1968 | Kuth et al. ............... | 8/42 |
| 4,079,028 | 3/1978 | Emmons et al. ............... | 260/29.6 NR |
| 4,155,892 | 5/1979 | Emmons et al. ............... | 260/29.2 TN |
| 4,499,233 | 2/1985 | Tetenbaum et al. ............... | 524/591 |
| 4,943,299 | 7/1990 | Schulze et al. ............... | 8/610 |
| 5,023,309 | 6/1991 | Kruse et al. ............... | 528/49 |
| 5,266,622 | 11/1993 | Mazanek et al. ............... | 524/131 |

FOREIGN PATENT DOCUMENTS

| | | |
|---|---|---|
| 1177988 | 11/1984 | Canada . |
| 495373 | 7/1992 | European Pat. Off. . |
| 3630319 | 3/1988 | Germany . |
| 19523837 | 2/1997 | Germany . |

*Primary Examiner*—Patrick D. Niland
*Attorney, Agent, or Firm*—Joseph C. Gil; Thomas W. Roy; Diderico van Eyl

[57] ABSTRACT

A thickener composition for thickening aqueous compositions which contains a) a water soluble or water dispersible thickener containing urethane groups, b) a non-ionic aromatic or alkyl-substituted aromatic emulsifier and c) a compound corresponding to formula I $$R_2-[(Q_2-)_tH]_u \qquad (I)$$

wherein $R_2$ represents an optionally branched and unsaturated aliphatic radical having 6 to 22 carbon atoms, a cycloaliphatic radical having 6 to 10 carbon atoms or a heterocyclic radical having 5 to 12 ring atoms, as obtained by removing the active hydrogen from a hydroxyl, amino, carboxylic acid or amide group, $Q_2$ represents a $C_2$–$C_4$ alkylene oxide unit, t has a value from 1 to 30 and u has a value from 1 to 10, and d) optionally further additives.

8 Claims, No Drawings

POLYURETHANE-BASED THICKENER COMPOSITIONS AND THEIR USE FOR THICKENING AQUEOUS COMPOSITIONS

BACKGROUND OF THE INVENTION

Field of the Invention

The present invention relates to new thickener compositions for thickening aqueous compositions, which are characterized by a particularly low viscosity combined with a good thickening action.

Description of the Prior Art

Polyurethane-based thickeners for aqueous systems have been described, e.g., in DE-A 1,444,243, DE-A 3,630,319, EP-A-0,031,777, EP-A-0,307,775, EP-A-0,495,373, U.S. Pat. No. 4,079,028, U.S. Pat. No. 4,155,892, U.S. Pat. No. 4,499,233 and U.S. Pat. No. 5,023,309.

A common feature of these prior art thickeners is the simultaneous presence of (i) hydrophilic segments in an amount of at least 50 wt. %, (ii) hydrophobic segments in an amount of at most 10 wt. %, and (iii) urethane groups. The term "hydrophilic segments" means polyether chains having at least five chain members in which the alkylene oxide units contain at least 60 mole % of ethylene oxide units. The term "hydrophobic segments" means hydrocarbon segments having at least six carbon atoms. These definitions apply to component a) of the compositions according to the invention.

These polyurethane thickeners are suitable as additives for adjusting the rheological properties of aqueous compositions such as automotive and industrial paints, rendering coats and paints, printing inks and textile colorants, pigment printing pastes, pharmaceutical and cosmetic preparations, plant protection formulations and filler dispersions.

Although the prior art polyurethane thickeners may be used for many applications, they have a basic disadvantage, i.e., too high an inherent viscosity in the form of their aqueous solution, which makes it difficult to incorporate them into the aqueous compositions.

Many attempts have been made in the past to reduce the inherent viscosity of these thickeners. Attempts have been made during the production stage of these thickeners to reduce the inherent viscosity, for example, by reducing the molecular weight. However, within a series of homologs this has the effect of reducing the thickener action.

The obvious step of reducing the viscosity of the aqueous solutions by dilution with water obviously has the disadvantage of reducing the concentration of the active constituents, which lowers the thickening action for the same overall amount of thickener.

One convenient method for reducing the inherent viscosity of the aqueous polyurethane thickener solutions is to add water miscible solvents such as water soluble monohydric or polyhydric alcohols. A disadvantage of this method, which is very effective, is that it has an adverse effect on the environmental compatibility of the aqueous compositions. In addition, the amount of solvents that have to be used to achieve a desired viscosity is often relatively high. Relatively large amounts of solvents can also cause a deterioration in the application properties of the aqueous compositions, for example, the coating properties or the stability.

Another method for reducing the viscosity of aqueous solutions of polyurethane thickeners is to add emulsifiers such as alkoxylated alcohols or phenols. A disadvantage of these additives is that they have to be used in high concentrations in order to achieve a sufficient reduction in the inherent viscosity of the thickener. Also, with this method it has not previously been possible to reduce the inherent viscosity of the thickeners to the desired value, especially in the case of highly active thickeners.

An object of the present invention is to provide new polyurethane-based thickener compositions for aqueous compositions, which in the form of their aqueous solutions or dispersions have a significantly reduced inherent viscosity and have at least as good a thickening action as analogous systems of the prior art.

This object was surprisingly achieved with the thickener compositions described hereinafter.

SUMMARY OF THE INVENTION

The present invention relates to a thickener composition for thickening aqueous compositions which contains
a) a water soluble or water dispersible thickener containing urethane groups,
b) a non-ionic aromatic or alkyl-substituted aromatic emulsifier corresponding to formula II
Component b) is selected from compounds corresponding to the formula II $$R\text{—}[O\text{—}(Q_1)_x\text{—}H]_y \qquad (II)$$

wherein
R represents an aromatic and/or an alkyl-substituted aromatic hydrocarbon radical having 6 to 50, preferably 6 to 40 carbon atoms, which may optionally contain inert substituents,
$Q_1$, represents $C_2$–$C_4$ alkylene oxide units, preferably ethylene oxide units and/or propylene oxide units,
x has a value from 1 to 300, preferably 5 to 100, and more preferably 10 to 30, and
y has a value from 1 to 20, preferably 1 to 10, and more preferably 1 to 4.
c) a compound corresponding to formula I $$R_2\text{—}[(Q_2\text{—})+H]_u (I)$$

wherein
$R_2$ represents an optionally branched and/or unsaturated aliphatic radical having 6 to 22 carbon atoms, a cycloaliphatic radical having 6 to 10 carbon atoms or a heterocyclic radical having 5 to 12 ring atoms, as obtained by removing the active hydrogen from a hydroxyl, amino, carboxylic acid or amide group,
$Q_2$ represents a $C_2$–$C_4$ alkylene oxide unit,
t has a value from 1 to 30 and
u has a value from 1 to 10,
d) further additives (optionally).

The invention also relates to the use of this thickener composition in aqueous compositions selected from aqueous automotive and industrial paints, rendering materials and paints, printing inks and textile colorants, pigment printing pastes, aqueous pharmaceutical and cosmetic preparations, plant protection formulations, filler and pigment dispersions, detergent preparations, adhesives, waxes and polishes, and for petroleum extraction.

DETAILED DESCRIPTION OF THE INVENTION

Component a) of the compositions according to the invention is selected from known polyurethane thickeners, preferably those containing at least 50 wt. % of hydrophilic segments and at most 10 wt. % of hydrophobic segments. Examples include the thickening agents described in U.S. Pat. Nos. 4,079,028, 4,155,892, 4,499,233 and 5,023,309 (all of which are herein incorporated by reference), wherein Suitable starter molecules for preparing component b) are monofunctional and polyfunctional phenols corresponding to formula II, preferably those corresponding to the following formulas:

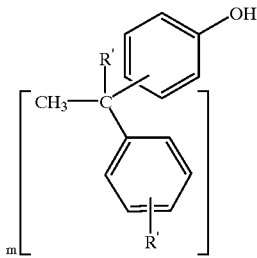

wherein
m has an average value of 0.5 to 2.8 and
$R^1$ represents hydrogen or methyl and

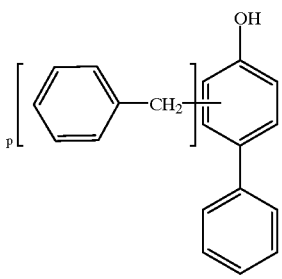

wherein
has an average value of 0.5 to 2.8.

Component c) is preferably selected from compounds corresponding to formula I

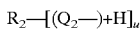

wherein
$R_2$ represents an optionally branched and/or unsaturated aliphatic radical having 6 to 22, preferably 6 to 16, more preferably 8 to 16 carbon atoms and most preferably 8 to 12 carbon atoms, a cycloaliphatic radical having 6 to 10 carbon atoms or a heterocyclic radical having 5 to 12, preferably 5 to 7 ring atoms, as obtained by removing the active hydrogen from a hydroxyl, amino, carboxylic acid or amide group,
$Q_2$ represents $C_2$–$C_4$ alkylene oxide units, preferably ethylene oxide units and/or propylene oxide units,
t has a value from 1 to 30, preferably 2 to 20 and more preferably 4 to 14 and
u has a value 1 to 10, preferably 1 to 6, and more preferably 1 or 2.

Component c) is selected from the alkylation products of suitable, known starter molecules. Examples of alkylene oxides being include ethylene oxide, propylene oxide and the isomeric butylene oxides, preferably ethylene oxide or mixtures containing ethylene oxide. It is possible to use different alkylene oxides in succession so as to form different polyether blocks.

Suitable starter molecules for component c) include n-hexanol, n-octanol, isooctanol, n-nonanol, isononanol, n-decanol, iso-undecanol, undecanol, n-dodecanol, tetradecanol, hexadecanol and mixtures thereof, such as those in industrial syntheses or from natural products. Other examples include cyclohexanol, methylcyclohexanol, hydroxytetraline, n-hexylamine, n-octylamine, n-dodecylamine, dodecanoic acid amide, caprolactam etc.

In a preferred embodiment of the present invention component c) is selected from compounds corresponding to formula III

wherein
$R_2$ represents a linear aliphatic radical having 6 to 16, preferably 8 to 16 carbon atoms, more preferably 10 to 14 atoms,
v has a value from 3 to 10 and
w has a value from 0 to 6,
v+w has a value of 3 to 16, preferably 8 to 14, more preferably 8 to 10.

In another preferred embodiment of the present invention component c) is selected from compounds corresponding to formula IV

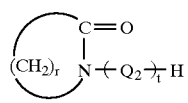

wherein
$Q_2$ represents ethylene oxide and/or propylene oxide,
r has a value from 2 to 20 and
t has a value from 1 to 30.

Additives d), which may optionally be used, include polyhydric alcohols such as propylene glycol, optionally in aqueous mixtures, which may be used, inter alia, to formulate the individual components.

In the thickener compositions according to the invention component b) is preferably present in an amount of 0.5 to 80, more preferably 5 to 50 and most preferably 10 to 30 wt. %, based on the total solids of components a), b) and c). Component c) is preferably present in an amount of 0.5 to 80, more preferably 1 to 50 and most preferably 1 to 40 wt. %, based on the total solids of components a), b) and c). The total amount of the components b) and c) is preferably at most 90 wt. %, more preferably at most 70 wt. % and most preferably at most 50 wt. %, based on the total solids of components a), b) and c). Total solids means the total weight of the aqueous-free individual components a), b) and c).

In addition to components a), b) and c) that are essential to the invention, additives d) may also be present. The amount of these additives is at most 30 wt. %, based on the total solids of components a), b) and c).

The thickener compositions according to the invention may be prepared in a known manner. For example, components b) and c) may be added successively while stirring and optionally heating to polyurethane thickener a), which may optionally dissolved in water. It is also possible to prepare a mixture of components b) and c), which is then added to polyurethane thickener a), which may optionally dissolved in water. In this connection it is possible to use known solvents and/or diluents as component d) to improve the miscibility of the individual components.

Another embodiment for preparing the compositions according to the invention is to add components b) and c), and optionally water, to polyurethane thickener a) immediately after its preparation. This method is particularly preferred since it has economic advantages over the other methods.

The compositions according to the invention are generally aqueous solutions or dispersions having a solids content of 10 to 90 wt. %, preferably 30 to 70 wt. % and more preferably 40 to 50 wt. %. In determining the solids content the term "solids" means the solids present in components a), b), c) and d). In the thickener composition the weight ratio of component a) to the sum of the components b) and c) is 3:1 to 1:3 and the weight ratio of component b) to component c) is 2:1 to 1:8.

The inherent viscosity of the compositions according to the invention can be determined by known methods, for example, in a Haake VT 500 rotational viscometer or in a Brookfield viscometer. The viscosity may vary within broad limits. However, the flow properties of the compositions are preferably such that they can be poured, pumped, etc., without any difficulty. The viscosity, measured at $10.3 s^{13\ 1}$ and 23° C., is 100 to 60,000 mPa.s, preferably 100 to 20,000 mPa.s and more preferably 100 to 10,000 mPa.s.

Due to their relatively low inherent viscosity, the compositions according to the invention may also be added in concentrated form for their use according to the invention. It is particularly noteworthy in this connection that the thickening action of the thickeners according to the invention is not reduced, or only insignificantly reduced, despite the comparatively sharply reduced inherent viscosity of these thickeners.

A further advantage of the compositions according to the invention is their compatibility with the aqueous compositions to be thickened, e.g., emulsion paints, which facilitates the incorporation of the thickeners, and at the same time the so-called maturation time of the resulting thickened compositions, i.e., the time to reach the maximum possible viscosity is significantly reduced.

The compositions according to the invention are suitable for thickening aqueous or predominantly aqueous compositions such as paints, printing inks and pigment pastes, filler dispersions and pigment dispersions, textile, leather and paper additives, oil extraction preparations, detergents, adhesives, waxes and polishes, formulations for pharmaceutical and veterinary purposes, plant protection preparations and cosmetic articles. The water itself may also be thickened with the polyurethane thickeners according to the invention so that further additives may be added, or so that the water itself can be added to aqueous preparations.

The thickener compositions according to the invention are suitable not only for thickening purely aqueous compositions, but also those compositions that contain organic solvents or other volatile additives, for example, polyhydric alcohols. The aqueous compositions to be thickened may contain known additives such as defoaming agents, flow control agents, fillers and pigments.

Examples of aqueous compositions that can be thickened according to the invention include aqueous polyacrylate dispersions, aqueous dispersions of copolymers of olefinically unsaturated monomers, aqueous polyvinyl acetate dispersions, aqueous polyurethane dispersions, aqueous polyester dispersions, two-component paints, and especially ready-to-use compositions containing these dispersions.

When the compositions according to the invention are used to thicken latex paints, this often leads to improved flow behavior of these compositions and to an improved surface finish of the resulting coatings. A further advantage of the compositions according to the invention is that their use in pigment-containing and/or filler-containing latex paints often leads to an improved wettability of these solids, which in turn facilitates the dispersion process, i.e., the production of the ready-to-use latex paints. Coatings produced using emulsion paints thickened according to the invention are also characterized by an enhanced gloss.

The invention is further illustrated but is not intended to be limited by the following examples in which all parts and percentages are by weight unless otherwise specified.

EXAMPLES

Examples 1 to 5

The thickener from Example 5 of DE-A 4,327,481 was used.

To 26 g of the polyurethane thickener a) were added as component b) various amounts of a non-ionic surfactant corresponding to the formula

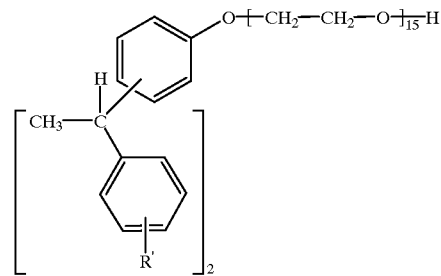

and as component c) various amounts of a low molecular weight polyether $R_{9-11}$—$EO_6$—$PO_{2.5}$ prepared from a 1:1 mixture of nonyl and undecyl alcohols ($R_{9-11}$) propylene oxide (PO) and ethylene oxide (EO), and water (up to 100 g). The mixtures were stirred for 30 minutes at 70° C. (500 revs/min), then for 8 hours at 50° C. before they were stored for 8 hours at room temperature. The viscosity of the resultant solutions was measured in a Haake VT500 viscometer, measurement body SV DIN, at 23° C. and $10.3\ s^{-1}$. The results are set forth in Table 1.

TABLE 1

| | Composition of the thickener composition (Wt. %, remainder water) | | | |
|---|---|---|---|---|
| Example No. | Thickener a) | Component b) | Component c) | Viscosity (mPa · s/23° C.) |
| 1 | 26 | 19 | 5 | 13850 |
| 2 | 26 | 14 | 10 | 10400 |
| 3 | 26 | 9 | 15 | 6800 |
| 4 | 26 | 7 | 17 | 5400 |
| 5 | 26 | 4 | 20 | 5100 |

EXAMPLES 6 to 10

The procedure of Examples 1 to 5 was repeated with the exception that either one or both of components b) and c) was not added. The results are set forth in Table 2 and demonstrate that neither component b) nor component c) was sufficient by itself to produce products having the low viscosity and storage stability of the thickeners according to the invention. Either the viscosity was too high (Example 7) or the mixtures were not storage stable (Examples 8 to 10).

TABLE 2

Composition of the thickener preparation (Wt. %, remainder water)

| Example No. | Thickener a) | Component b) | Component c) | Viscosity (mPa · s/ 23° C.) | Warm storage, 50° C. |
|---|---|---|---|---|---|
| 6 | 26 | — | — | Too high[2] (not measurable) | Not relevant |
| 7 | 26 | 24 | — | 30,500 | Satisfactory |
| 8 | 26 | — | 24 | 4000 | Separated into two layers at >40 C. |
| 9 | 28 | — | 22 | 6300 | |
| 10 | 30 | — | 20 | 11100 | |

2) > 60,000 mPa · s

EXAMPLES 11 to 15

The following examples demonstrate that the thickening action of component a) was not adversely affected by viscosity-reducing additives b) and c). The values fell within the known limits.

Measurement of thickening action

In each example 2 g of an aqueous solution of a thickener composition were added to 98 g of a commercially available polyacrylate dispersion (Dilexo RA3, available from Condea, Hamburg). In each example the concentration of polyurethane thickener a) was 2.5 wt. %, based on resin solids. The mixtures were stirred for 5 minutes at 2000 revs/min and the resulting homogeneous dispersions were stored for 3 hours at 23° C. The viscosity was then measured as described above. The results are set forth in Table 3.

TABLE 3

| Example No. | Thickener composition from Example No. | Thickening action Viscosity (mPa · s) (23° C.) |
|---|---|---|
| 11 | 7 (without component c) | 12400 |
| 12 | 2 | 12200 |
| 13 | 4 | 12600 |
| 14 | 9 | 12300 |
| 15 | 10 | 12500 |

EXAMPLES 16 to 24

The procedure of Example 1 was repeated with the exception that different compounds were used as component c). In all of the examples the ratio of components a), b) and c) was 26:12:12; the remaining 50 parts was water.

TABLE 4

Composition of the thickeners and thickening action

| Example No. | Composition of component c) | Viscosity mPa · s | Thickener action mPa · s/23° C. |
|---|---|---|---|
| 16 | Mixture Nonanol/undecanol 1:1/7EO | 10900 | 12700 |
| 17 | Tridecanol/4EO/1.5PO | 13800 | 12400 |
| 18 | Tridecanol/5EO/3PO | 12800 | 12500 |
| 19 | Isooctanol/6EO/4PO | 12900 | 12450 |
| 20 | Isooctanol/5EO/5PO | 10400 | 12300 |
| 21 | Nonanol/undecanol/ 1:1/5EO/5PO | 10000 | 12700 |
| 22 | Isodecanol/6EO/5PO | 13100 | 12400 |

TABLE 4-continued

Composition of the thickeners and thickening action

| Example No. | Composition of component c) | Viscosity mPa · s | Thickener action mPa · s/23° C. |
|---|---|---|---|
| 23 | 2-ethylhexanol/8PO/6EO | 26300 | 12200 |
| 24 (Comp) | 24 parts component b), without component c) | 30500 | 12500 |

EXAMPLES 25 to 34

The procedure of Examples 1 to 5 was repeated with the exception that a different thickener was used, i.e., the thickener from Example 79 of U.S. Pat. No. 4,079,028, except that hexamethylene diisocyanate was used instead of toluylene diisocyanate. The results are set forth in Table 5. Table 5 also sets forth the thickening action of the compositions according to the invention, which were measured as described in Examples 11 to 15. In all of the examples the ratio of components a), b) and c) was 26:12:12; the remaining 50 parts was water. Component b) was the same as in Example 1. The examples demonstrate that the thickening action of component a) was not adversely affected by viscosity-reducing additives b) and c).

TABLE 5

Composition of the thickeners and thickening action

| Example No. | Composition of component c) | Viscosity mPa · s | Thickening action mPa · s/23° C. |
|---|---|---|---|
| 25 | Nonanol/undecanol 1:1/7EO | 3300 | 9300 |
| 26 | Tridecanol/4EO/1.5PO | 3900 | 9100 |
| 27 | Tridecanol/5EO/3PO | 3600 | 9000 |
| 28 | Isooctanol/6EO/4PO | 3700 | 9400 |
| 29 | Isodecanol/5EO/5PO | 3200 | 9250 |
| 30 | Nonanol/undecanol 1:1/5EO/5PO | 2800 | 9150 |
| 31 | Isodecanol/6EO/5PO | 5200 | 9100 |
| 32 | 2-ethylhexanol/8PO/6EO | 6900 | 9300 |
| 33 | Nonanol/undecanol 1:1/6EO/2.5PO | 2700 | 9200 |
| 34 (Comp) | 24 parts component b), without component c) | 8250 | 9200 |

EXAMPLES 35 to 37

Examples 25–33 were repeated with the exception that different compounds were used as component b). In all of the examples the ratio of components a), b) and c) was 26:12:12; the remaining 50 parts was water. Component c) was the same as in Example 1. The examples demonstrate that the thickening action of component a) was not adversely affected by viscosity-reducing additives b) and c). The results are set forth in Table 6.

TABLE 6

Composition of the thickeners and thickening action

| Example No | Component b) | Viscosity mPa · s | Thickener action mPa · s/23° C. |
|---|---|---|---|
| 35 | Borchigen DFN (aralkylphenol/14EO) | 3000 | 9250 |

TABLE 6-continued

Composition of the thickeners and thickening action

| Example No | Component b) | Viscosity mPa · s | Thickener action mPa · s/23° C. |
|---|---|---|---|
| 36 | Component b) from Example 1, but with 2.2 moles of styrene per mole of phenol and 16EO | 3500 | 9300 |
| 37 | Nonylphenol/10EO | 2900 | 9100 |

EXAMPLES 38 to 49

The procedure of Example 1 was repeated with the exception that the following compounds were used as component b):

I. Condensation product of 2.2 moles of benzyl chloride and 1 mole of hydroxybisphenyl, reacted with 15 moles of EO
II. Condensation product of 2.8 moles of styrene and 1 mole of phenol, reacted with 17 moles of ethylene oxide
III. Condensation product of 2 moles of styrene and 1 mole of phenol, reacted with 12 moles of ethylene oxide
IV. Condensation product of 2.8 moles of vinyl toluene with I mole of phenol, reacted with 20 moles of EO
V. Condensation product of 1.8 moles of styrene with 1 mole of phenol, reacted with 14 moles of EO
VI. Condensation product of 2 moles of styrene with 1 mole of phenol, reacted with 20 moles of EO and 4 moles of PO
VII. Condensation product of 2 moles of styrene with 1 mole of phenol, reacted with a mixture of 13 moles of EO and 4 moles of PO
VIII. Condensation product of 1.8 moles of α-methyl styrene and 1 mole of phenol, reacted with 16 moles of EO These compounds were used in the amounts set forth in Table 7 to prepare the compositions according to the invention.

TABLE 7

| Example | Component b) | Component c) | Viscosity mPa · s | Thickener action mPa · s/23° C. |
|---|---|---|---|---|
| 38 | 12 parts I | 12 parts component c) from Example 1 | 11100 | 12300 |
| 39 | 12 parts II | 12 parts n-hexanol/4 EO | 12000 | 11800 |
| 40 | 14 parts I | 10 parts n-hexanol/4 EO | 13600 | 11900 |
| 41 | 10 parts V | 14 parts n-octanol/4 EO/2 PO | 10500 | 12100 |
| 42 | 14 parts VI | 10 parts caprolactam/4 PO | 14200 | 12400 |
| 43 | 12 parts IV | 12 parts n-nonanol/4.5 EO/2.5 PO | 12200 | 12500 |
| 44 | 20 parts I | 4 parts n-hexanol/3 EO/1 PO | 21600 | 12700 |
| 45 | 13 parts III | 11 parts n-octanol/4 EO | 12900 | 12200 |
| 46 | 12 parts VII | 12 parts n-hexanol/5 EO | 11800 | 12500 |
| 47 | 12 parts VIII | 12 parts n-dodecanol/5 EO/2 PO | 13400 | 12700 |
| 48 | 14 parts I | 10 parts n-hexadecanol/8 EO/3 PO | 15100 | 12400 |
| 49 (comparison) | 24 parts of component b) from Example 1 | | 30500 | 12500 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A thickener composition for thickening aqueous compositions which contains
   a) a water soluble or water dispersible thickener containing urethane groups,
   b) a non-ionic aromatic or alkyl-substituted aromatic emulsifier selected from compounds corresponding to the formula II $$R-[O-(Q_1)_x-H]_y \quad \text{(II)}$$

wherein
   R represents an aromatic and an alkyl-substituted aromatic hydrocarbon radical having 6 to 50, which may optionally contain inert substituents;
   $Q_1$ represents $C_2-C_4$ alkylene oxide units;
   x has a value from 1 to 300; and
   y has a value from 1 to 20;
   c) a compound corresponding to formula I $$R_2-[(Q_2-)_tH]_u \quad \text{(I)}$$

wherein
   $R_2$ represents an optionally branched and unsaturated aliphatic radical having 6 to 22 carbon atoms, a cycloaliphatic radical having 6 to 10 carbon atoms or a heterocyclic radical having 5 to 12 ring atoms, as obtained by removing the active hydrogen from a hydroxyl, amino, carboxylic acid or amide group,
   $Q_2$ represents a $C_2-C_4$ alkylene oxide unit,
   t has a value from 1 to 30 and
   u has a value from 1 to 10,
   d) optionally further additives.

2. The thickener composition of claim 1 wherein component b) comprises a compound corresponding to formula II $$R-[O-(Q_1)_x-H]_y \quad \text{(II)}$$

wherein
R represents an aromatic and/or an alkyl-substituted aromatic hydrocarbon radical having 6 to 50 carbon atoms, which may optionally contain inert substituents,
$Q_1$ represents a $C_2-C_4$ alkylene oxide unit,
x has a value from 1 to 300 and
y has a value from 1 to 20.

3. The thickener composition of claim 1 wherein component c) comprises a compound corresponding to formula III $$R_2-[O-EO_v-PO_w)-H] \quad \text{(III)}$$

wherein
  $R_2$ represents a linear aliphatic radical having 6 to 16 carbon atoms, preferably 10 to 14 atoms, more preferably 10 to 14 atoms,
  v has a value from 3 to 10 and
  w has a value from 0 to 6,
  v+w has a value of 3 to 16, preferably 8 to 14, more preferably 8 to 10.

4. The thickener composition of claim 2 wherein R represents a compound corresponding to the formula

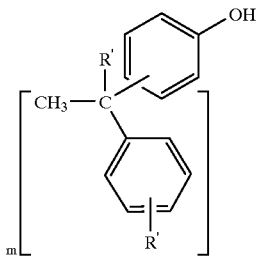

wherein
  m has an average value of 0.5 to 2.8 and
  R' represents hydrogen or methyl or

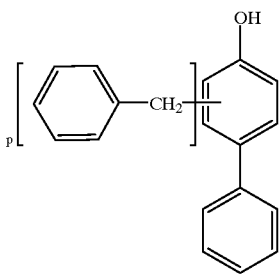

wherein
  p has an average value of 0.5 to 2.8.

5. The thickener composition of claim 1 wherein the weight ratio of component a) to the sum of the components b) and c) is 3:1 to 1:3.

6. The thickener composition of claim 1 wherein the weight ratio of component b) to component c) is 2:1 to 1:8.

7. A thickener composition for thickening aqueous compositions which contains
  a) a water soluble or water dispersible thickener containing urethane groups,
  b) a non-ionic aromatic or alkyl-substituted aromatic emulsifier selected from compounds corresponding to the formula II $$R\!-\!\![O\!-\!(Q_1)_x\!-\!H]_y \qquad (II)$$

wherein
  R represents an aromatic and an alkyl-substituted aromatic hydrocarbon radical having 6 to 50, which may optionally contain inert substituents,
  $Q_1$ represents $C_2$–$C_4$ alkylene oxide units,
  x has a value from 1 to 300, and
  y has a value from 1 to 20;
  c) a compound corresponding to formula IV

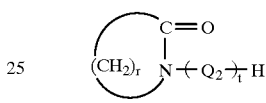

wherein
  $Q_2$ represents ethylene oxide and/or propylene oxide,
  r has a value from 2 to 20 and
  t has a value from 1 to 30.

8. The thickener composition of claim 1, wherein R comprises an hydrocarbon radical having 6 to 50 or 6 to 40 carbon atoms,
  $Q_1$ comprises $C_2$–$C_4$ an alkylene oxide units component selected from the group consisting of ethylene oxide units and propylene oxide units;
  x comprises a value from 5 to 100 or 10 to 30, and y has a value from 1 to 10 or preferably 1 to 4.

* * * * *